United States Patent
Oswald et al.

(10) Patent No.: US 6,635,177 B2
(45) Date of Patent: Oct. 21, 2003

(54) RECLAIMING WATER AND USABLE BRINE CONCENTRATE FROM DOMESTIC SEWAGE

(75) Inventors: William J. Oswald, Concord, CA (US); Franklin Bailey Green, Kensington, CA (US); Ezio Bracco, Savona (IT)

(73) Assignees: The Regents of the University of California, Oakland, CA (US); Expertise SRL, Vado Ligure (IT)

( * ) Notice: Subject to any disclaimer, the term of this patent is extended or adjusted under 35 U.S.C. 154(b) by 82 days.

(21) Appl. No.: 10/083,222

(22) Filed: Oct. 24, 2001

(65) Prior Publication Data

US 2002/0153303 A1 Oct. 24, 2002

Related U.S. Application Data

(60) Provisional application No. 60/243,545, filed on Oct. 25, 2000.

(51) Int. Cl.$^7$ .............................. C02F 3/28; C02F 3/32; C02F 3/34; A01H 13/00
(52) U.S. Cl. ...................... 210/602; 210/603; 210/605; 47/1.4
(58) Field of Search ................................. 210/602, 603, 210/605, 610, 611, 620, 631; 47/1.4

(56) References Cited

U.S. PATENT DOCUMENTS

| | | |
|---|---|---|
| 212,023 A | 2/1879 | Maurer |
| 2,638,444 A | 5/1953 | Kappe |
| 3,444,647 A | 5/1969 | Takahashi |
| 3,839,198 A | 10/1974 | Shelef |
| 3,933,628 A | 1/1976 | Varani |
| 4,005,546 A | 2/1977 | Oswald |
| 4,162,976 A | 7/1979 | Monson |
| 4,209,388 A | 6/1980 | DeFraites |
| 4,615,807 A | 10/1986 | Haines et al. |
| 4,632,758 A | 12/1986 | Whittle |

(List continued on next page.)

FOREIGN PATENT DOCUMENTS

| FR | 2587326 | 3/1987 |
|---|---|---|
| WO | PCT/US01/46107 | 10/2001 |

OTHER PUBLICATIONS

U.S. patent application Ser. No. 09/552,576, Oswald et al., filed Apr. 19, 2000.

U.S. patent application Ser. No. 10/115,838, Oswald et al., filed Apr. 2, 2002.

(List continued on next page.)

Primary Examiner—Fred Prince
(74) Attorney, Agent, or Firm—Pennie & Edmonds LLP

(57) ABSTRACT

A method of processing sewage. Non-biodegradable solids are first removed from the sewage for separate disposal. The sewage is then introduced to the bottom of a fermentation cell designed to optimize sedimentation and methane fermentation of settleable organic solids, most of which settle in the fermentation cell. Sulfate-reducing micro-organisms that release sulfides are growing in the fermentation cell. The sulfides released combine with multivalent metal particles in the sewage to form insoluble particles, a portion of which settles in the fermentation cell. The remaining metal sulfides, other suspended solids, microorganisms, nutrients, and pathogens in the sewage are then removed by natural means followed by Dissolved Air Flotation, Slow Sand Filtration and disinfection. Metal ions that escaped sedimentation in the fermentation cell are adsorbed by microorganisms that have a strong negative surface charge. Finally, reverse osmosis is carried out to produce purified water and a high-salinity concentrate. The purified water and the high-salinity concentrate, being substantially free of toxic multivalent metal particles, can be used respectively for safe human consumption and for cultivation of halophilic microalgae.

12 Claims, 1 Drawing Sheet

U.S. PATENT DOCUMENTS

| | | | |
|---|---|---|---|
| 4,789,478 A | * 12/1988 | Revis et al. | 210/611 |
| 4,959,084 A | 9/1990 | Wolverton et al. | |
| 4,966,096 A | 10/1990 | Adey | |
| 4,981,593 A | 1/1991 | Priestley et al. | |
| 4,997,568 A | 3/1991 | Vandervelde et al. | |
| 5,011,604 A | 4/1991 | Wilde et al. | |
| 5,097,795 A | 3/1992 | Adey | |
| 5,254,252 A | 10/1993 | Drenner | |
| 5,298,163 A | * 3/1994 | Ehlinger | 210/603 |
| 5,364,529 A | 11/1994 | Morin et al. | |
| 5,500,123 A | * 3/1996 | Srivastava | 210/603 |
| 5,500,306 A | 3/1996 | Hsu et al. | |
| 5,531,898 A | 7/1996 | Wickham | |
| 5,534,141 A | 7/1996 | McAnaney et al. | |
| 5,545,326 A | 8/1996 | Petering | |
| 5,599,451 A | 2/1997 | Gulot | |
| 5,616,241 A | 4/1997 | Khudenko | |
| 5,624,564 A | 4/1997 | Blum | |
| 5,660,730 A | * 8/1997 | Lucchese et al. | 210/611 |
| 5,707,513 A | 1/1998 | Jowett et al. | |
| 5,744,041 A | 4/1998 | Grove | |
| 5,773,526 A | 6/1998 | Van Dijk et al. | |
| 5,782,950 A | 7/1998 | Kanitz et al. | |
| 5,783,071 A | 7/1998 | Guy | |
| 5,792,355 A | 8/1998 | Desjardins | |
| 5,820,759 A | 10/1998 | Stewart et al. | |
| 5,861,095 A | 1/1999 | Vogel et al. | |
| 5,863,433 A | 1/1999 | Behrends | |
| 5,922,204 A | * 7/1999 | Hunter et al. | 210/603 |
| 5,932,099 A | 8/1999 | Cote et al. | |
| 5,976,372 A | * 11/1999 | Vesterager | 210/603 |
| 5,980,739 A | 11/1999 | Jowett et al. | |
| 5,992,317 A | 11/1999 | Hummel et al. | |
| 6,174,433 B1 | 1/2001 | Futami | |
| 6,203,700 B1 | 3/2001 | Rose et al. | |
| 6,203,702 B1 | 3/2001 | Sheaffer | |

OTHER PUBLICATIONS

Green et al., *Energetics of Advanced Integrated Wastewater Pond Systems*, 1995, Wat. Sci Tech. vol. 31, No. 12, pp. 9–20.

Green et al., *Methane Fementation, Submerged Gs Collection, and The Fate of Carbon in Advanced Integrated Wastewater Pond Systems*, 1995, Wat. Sci. Tech. vol. 31, No. 12, pp–55–65.

Green et al., *Advanced Integrated Wastewater Pond Systems for Nitrogen Removal*, 1996, Wat. Sci., Tech. vol. 33, No. 7, pp. 207–217.

W.J. Oswald, *Ponds in the Twenty–First Century*, 1995, Wat. Sci. Tech. vol. 31, No. 12, pp. 1–8.

William J. Oswald, *Advanced Integrated Wastewater Pond Systems*, Nov. 5–8, 1990, Supplying Water and Saving the Environment for Six Billion People/Sessions from 1990 ASCE Convention EE Div/ASCE, San Francisco, CA.

Downing et al., *Low Cost Reclamation Using the Advanced Integrated Wastewater Pond Systems Technology and Reverse Osmosis*, 2002, Water Science and Technology, vol. 45 No. 1 pp. 117–125.

Yakup Nurdogan and William J. Oswald, *Enhanced Nutrient Removal in High–Rate Ponds*, 1995, Wat. Sci. Tech. vol. 31, No. 12, pp. 33–43, 1995.

Oswald et al., *Performance of Methane Fermentation Pits in Advanced Integrated Wastewater Pond Systems*, 1994, Wat. Sci. Tech. vol. 30, No. 12, pp. 2987–295.

William J. Oswald, *Introduction to Advanced Integrated Wastewater Ponding Systems*, 1991, Wat. Sci. Tech., vol. 24, No. 5, pp. 1–7, 1991.

Photograph (taken 1941) of a human swimmer in an air trap submerged in the Wakulla River at Wakulla Springs, Florida reprinted in National Geographic "Swimsuits: 100 years of pictures," 2003.

* cited by examiner

RECLAIMING WATER AND USABLE BRINE CONCENTRATE FROM DOMESTIC SEWAGE

This application claims priority under 35 U.S.C. §119 (e) to U.S. provisional patent application No. 60/243,545, filed Oct. 25, 2000, which is hereby incorporated by reference in its entirety.

BRIEF DESCRIPTION OF THE INVENTION

The present invention relates generally to treatment of sewage. More particularly, the present invention relates to a method of reclaiming water and usable and safely disposable brine concentrate from domestic sewage.

BACKGROUND OF THE INVENTION

A household water supply usually contains several hundred milligrams per liter (mg/L) of minerals in the form of cations (e.g., sodium, magnesium and calcium, etc.) and anions (e.g., chloride, sulfate and bicarbonate, etc.). Subjected to the multiple uses in a home, the used water becomes a suspension of bathroom and kitchen wastes along with laundry wastes and cleaning compounds of multiple origins. Solvents, pigments, and pesticides are often disposed "down the drain." In addition to these substances, the used water also contain microgram amounts of several minerals (e.g., copper, cadmium, zinc, nickel, lead, chromium and iron) dissolved from household utensils, from copper and galvanized pipes and from lead and solder in the plumbing of older homes and apartment buildings. Domestic sewage will also contain minute, but increasing amounts, of antibiotics, hormones, and other health-related substances stemming from the growing medical and pharmaceutical industries.

In the prior art, domestic sewage can be reclaimed by using an activated sludge secondary treatment process followed by a microfiltration process and a reverse osmosis (RO) process. Water reclaimed by these prior art methods may re-enter the household water supply to be reused. Among these prior art processes, the reverse osmosis process is particularly important because it removes salt increment (i.e., the increase in total dissolved solids concentration associated with each use) from the treated water. Removal of salt increment is key for the sustainability of any multiple-pass water reuse scheme. If these added salts are not removed prior to reuse, the dissolved solids concentration of the reclaimed water will steadily increase, reducing reuse options. The reverse osmosis process is also important because it removes heavy metal ions from the reclaimed water and prevents heavy metal ions from re-entering the household water supply.

One problem of the prior art activated sludge/microfiltration/RO process is that it is costly. It has been estimated that a prior art activated sludge/microfiltration/reverse osmosis process uses more than 900 kWh of energy and costs more than U.S. $1200 to reclaim one million liters of sewage. Another problem of the prior art process is that heavy metals in the sewage will become highly concentrated along with other ions in the brine. The resultant high concentration of heavy metals adds to the hazards and costs of brine disposal.

In view of the foregoing, there exists a need for a wastewater treatment and reclamation process that is energy and cost effective.

SUMMARY OF THE INVENTION

The present invention provides a process of treating and reclaiming wastewater that is cost-effective. In addition, the end products of the reclamation process do not contain any toxic chemicals. Indeed, the end products of the reclamation process may be used in an economically and commercially beneficial way to help lower the cost of wastewater reclamation.

According to one embodiment of the invention, the treatment and reclamation process includes an intensely anaerobic methane producing process followed by a highly aerobic algal-based waste oxidation process, a Dissolved Air Flotation (DAF) process, a Slow Sand Filtration (SSF) and/or other filtration process (e.g., microfiltration, nanofiltration, ultrafiltration, etc.), a disinfection process and finally a Reverse Osmosis (RO) process. The anaerobic process precipitates most heavy metals as metal sulfides, and the aerobic algal-based wastewater treatment process entails the use of algae to adsorb the remaining heavy metals. The DAF process removes suspended solids and algae from the treated sewage. The SSF process ensures that substantially all suspended solids and microorganisms are removed from the treated sewage. The disinfection process eliminates microorganisms that are not already filtered out. Finally, the reverse osmosis process removes the remaining dissolved solids from the treated sewage to produce permeate water and a high salinity concentrate (e.g., brine). The permeate water is potable and the high salinity concentrate is substantially free of heavy metal ions. Preferably, the high salinity concentrate is used to cultivate halophilic algae, such as Dunaliella, which have a high commercial value. Thus the present invention provides for a method of reclaiming both water and high salinity concentrate from sewage. The present invention can also be used to reclaim other types of wastewater.

In furtherance of the present embodiment, the wastewater treatment and reclamation process removes calcium hardness from the sewage. Removal of calcium hardness "softens" water and minimizes the pretreatment required prior to reverse osmosis thus extending the useful life of the membranes used in the reverse osmosis process.

BRIEF DESCRIPTION OF THE DRAWING

Aspects of the present invention will be more readily apparent from the following description and appended claims when taken in conjunction with the accompanying drawing, in which:

DESCRIPTION OF THE PREFERRED EMBODIMENTS

Figure 1:
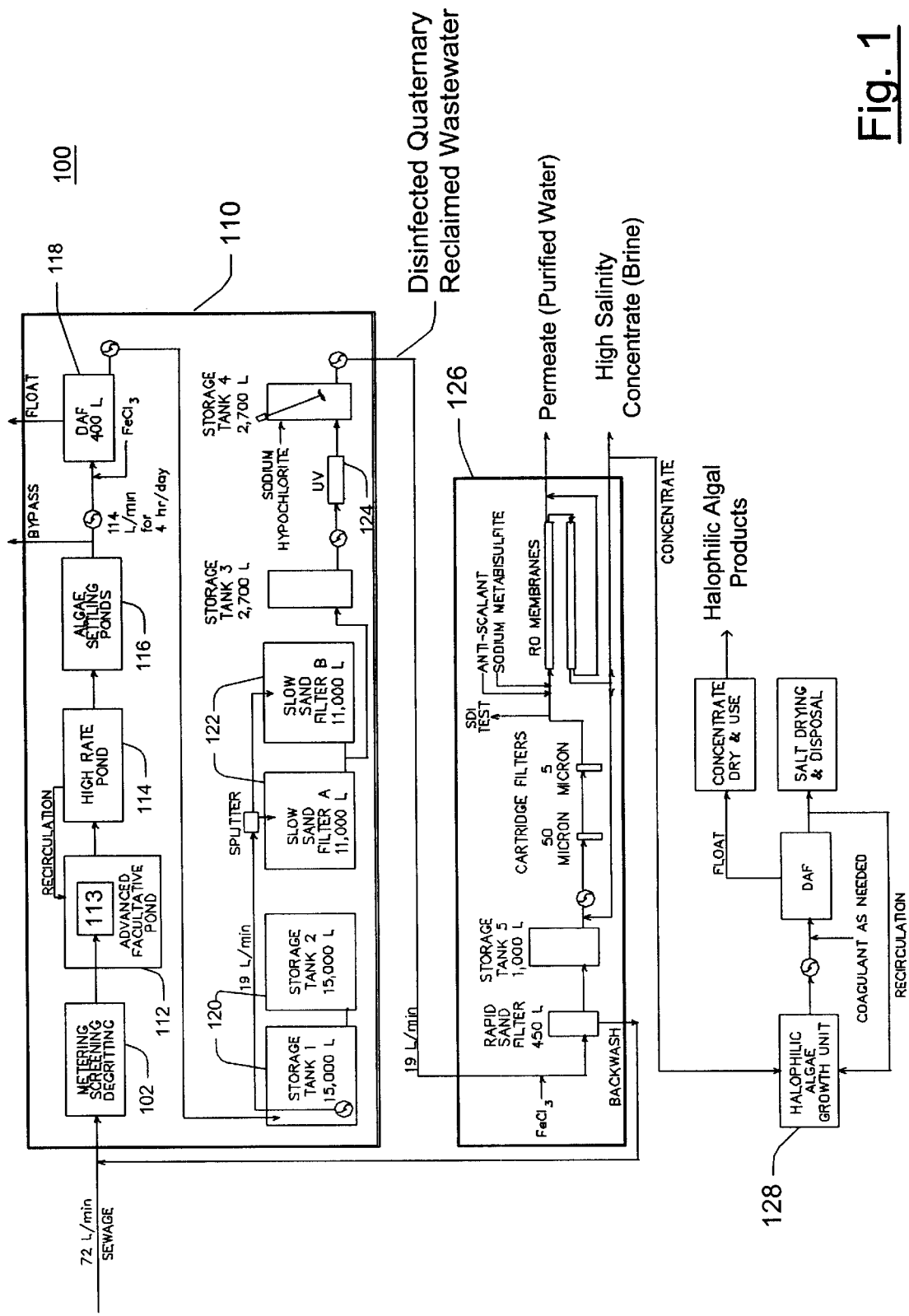
FIG. 1 is a block diagram illustrating a wastewater treatment process according to one embodiment of the present invention.

FIG. 1 is a block diagram illustrating the key steps of a wastewater treatment process 100 in accordance with one embodiment of the present invention. Some steps of the wastewater treatment process 100 are preferably carried out at an Advanced Integrated Wastewater Pond Systems® Facility 110. It should be noted herein that Advanced Integrated Wastewater Pond Systems® and AIWPS® are registered trademarks of Oswald Green, LLC of Concord, Calif., United States of America. An AIWPS® Facility is presently located at the Environmental Engineering and Health Sciences Laboratory of the University of California at Berkeley, in Richmond, Calif., United States of America.

With reference to FIG. 1, raw sewage first passes through a metering, screening and degritting station 102 where large and non-biodegradable solids are removed for separate disposal. The large and non-biodegradable solids are typically disposed by burial.

The sewage is then introduced into one or more five to six meter deep isolated fermentation cells 113 (sometimes called In-Pond Digesters when methane-rich biogas is collected), which in the present embodiment are constructed at the bottom of a primary facultative pond 112 and which are designed for optimal sedimentation and methane fermentation of settleable organic solids. According to the present embodiment, the fermentation cells 113 are protected on all sides by berms or walls that prevent intrusion of any oxygen-containing water. Under their high organic loading and with oxygen prevented from intruding, the fermentation cells 113 become extremely anaerobic, fostering the growth of archaea and sulfate-reducing organisms (e.g., facultative heterotrophs) that release sulfides. The released sulfides quickly combine with the multivalent metal ions in the sewage to form metal sulfides, which are insoluble. By passing all incoming sewage through such fermentation cells 113, most metal ions combine with sulfides and are precipitated to remain within the sludge of the fermentation cells indefinitely. Metal ions that may be present in the sewage may include copper, cadmium, zinc, nickel, lead, chromium, and iron. With the exception of copper ions, which are sometimes monovalent, these metal ions are multivalent and readily combine with sulfides released by the sulfate-reducing microorganisms. Fermentation cells and the methane fermentation process are described in greater detail in co-pending United States patent application entitled, "Method and Apparatus to Establish and Optimize Sedimentation and Methane Fermentation in Primary Wastewater Ponds" bearing application Ser. No. 09/552,576, which is hereby incorporated by reference in its entirety.

Because the primary anaerobic digestion process is designed to permit complete sludge digestion, very little solid residue remains in the fermentation cells 113, and sludge removal is only required after several decades. Preferably, sewage injected into the bottom of the fermentation cells has an overflow rate that is lower than the settling velocity of most particles (and parasite eggs) so that most of the particles remain in the fermentation cells until digested. Gases emitted from the fermentation cell are mainly methane ($CH_4$) and nitrogen ($N_2$) with very little $CO_2$. If in sufficient amounts, the methane-rich biogas can be captured and utilized to generate electricity. Where the amount of methane is insufficient to justify power generation, the methane is preferably flared to minimize its very substantial greenhouse effect or global warming potential.

With reference still to FIG. 1, sewage rising from the fermentation cells 113 enters a broad zone of semi aerobic water with highly aerobic water near or at its surface. This reactor is called a primary facultative pond or an Advanced Facultative Pond (AFP) 112. An aerobic condition at the surface of the AFP 112 is assured by adjusting the organic load to the rate at which algae in the surface can produce oxygen together with the amount of oxygenated water that is recycled to the AFP 112 from the next pond of the sequence, the High Rate Pond 114, which in the present embodiment is a shallow, aerobic, paddle-wheel-mixed, raceway pond. In rare instances of intensely cloudy weather, injection type aerators floating in the AFP 112 can be activated to supplement dissolved oxygen concentrations near the surface of the AFP 112 to mitigate odor release.

With reference still to FIG. 1, the High Rate Pond (HRP) 114 is designed as an endless raceway that fosters growth of many species of green microalgae (e.g., Chlorella, Scenedesmus, Micractinium, etc.) that split water and release Oxygen radicals that combine to become $O_2$, dissolved oxygen (DO). The green microalgae, which are fast-growing and carry a strong negative charge on their surfaces, are used for adsorbing metal ions that escaped precipitation in the fermentation cells 113. Accordingly, by recirculating pond water containing young, fast-growing algae to the surface of the AFP 112, there is an opportunity for metals not removed in the fermentation cells 113 to be adsorbed and removed from the sewage flow together with the algae that settle to the bottom of the AFP 112. A fraction of the microalgae culture in the HRP 114 is recirculated to the upwind surface of the AFP 112 in order to transfer oxygen-producing and metal-adsorbing algae to the AFP 112.

When the HRP 114 is continuously gently mixed with a paddle wheel, some algae may grow large enough or become flocculated and may tend to settle to the bottom of an Algae Settling Pond (ASP) 116. Algae removed by natural sedimentation concentrate to about 3% solids at the bottom of the ASP 116. If the supernatant liquid is decanted, the remaining algal separation may be used as animal feed after pasteurization or as fertilizer after sufficient storage time to permit natural die away of any associated pathogenic bacteria. It is virtually impossible for parasite ova that may be in the original sewage to reach this stage of the process.

If natural algal separation is insufficient to meet government standards for suspended solids, the effluent from the ASP 116 can be subjected to Dissolved Air Flotation. In the present embodiment, the ASP effluent is coagulated, and most of the suspended solids are removed with a Dissolved Air Flotation (DAF) unit 118. The DAF process is used because of its effectiveness in removing algal suspended solids and its ability to produce an algal float with low water content. In one implementation, the DAF unit 118 has a volume of 450 L and is operated at 114 L/min for 4 to 5 hours daily. The DAF effluent produced during these runs filled two 15,000-L storage tanks. Flocculation and coagulation in the DAF unit 118 can be enhanced by the use of ferric chloride ($FeCl_3$), aluminum sulfate, or cationic polymers that are "Generally Recognized as Safe" (GRAS) for animal feed by the U.S. Department of Agriculture. Coagulants are dosed into the 5.1-cm diameter ASP effluent pipe 20 m upstream of the DAF unit 118, allowing for approximately 20 seconds of mixing. According to the present embodiment, ferric chloride is used because it provides a high level of turbidity and solids removal per unit chemical cost. In one specific embodiment, feric chloride is dosed at 44 mg/L as $FeCl_3$ during the first 730 hours of operation and at 66 mg/L thereafter.

With reference still to FIG. 1, the DAF effluent is conveyed to storage tanks 120. The DAF effluent in the storage tanks 120 is suitable for irrigation purposes.

According to the present embodiment, the water in the maturation pond 120 is further subjected treatment by two Slow Sand Filtration units 122 (and/or other filtration units such as microfiltration units, nanofiltration units, ultrafiltration units, etc). In one implementation, the SSF units 122 are constructed from two 3.05-m diameter, 2.1-m deep cross-linked polyethylene tanks, filled to a depth of one meter with filtration media. The base gravel layer was 30 cm of 1.9- to 1.25-cm round gravel topped by a 25-cm layer of pea gravel. These gravel layers covered a network of 7.5-cm diameter corrugated ABS perforated drain pipe. The gravel layers were then covered with a 46-cm layer of 30-mesh, silica, water filter sand. After 180 hours of system operation, layers of geotextile fabric were installed on top of the sand. This fabric, which may increase the interval between filter cleanings, is preferably Amoco Style 4512, a nonwoven polypropylene felted geotextile. The fabric is 3.3 mm thick and has a specific surface area of 16,424 $m^2/m^3$ and a porosity of 85%. Both sand filters were operated with a covering of between one and seven layers of fabric for the remainder of the test period. The SSF units 122 are operated in parallel at a total flow rate of nineteen liters per minute. A constant water depth of two meters (measured from the bottom of the tank) should be maintained in the SSFs. When the combined flow through the filters dropped below nineteen liters per minute, the filters may require cleaning. Filter cleaning intervals may range from five and ten days.

Effluent from the SSF units 122 is then subjected to treatment by a disinfection unit 124. In the present embodiment, the disinfection unit 124 is an Infilco-Degremont Model 1XS ultra-violet disinfection unit with a design flow of 26.5 liters per minute. At the 19-liter per minute flow used, the minimum dose delivered by the unit is 240 $mW/cm^2$ (excluding losses due to water turbidity), which exceeds the minimum 140–160 $mW/cm^2$ disinfection dose recommended by the California Department of Health Services. The effluent from the disinfection unit 124 is disinfected quaternary reclaimed wastewater. In the present embodiment, the disinfected quaternary reclaimed wastewater meets the most stringent government recycled/reclaimed water standards that are presently enforced.

Last but not least, effluent from the disinfection unit 124 is passed to a Reverse Osmosis unit 126. In the present embodiment, the RO unit 126 includes the following pretreatment processes: chlorine disinfection, pH adjustment, coagulation, rapid sand filtration, 50-micron cartridge filtration, 5-micron cartridge filtration, dechlorination, and antiscalant addition. Pretreatment chemicals are added via adjustable metering pumps at various dose points. The effectiveness of this pretreatment can be measured by the Silt Density Index (SDI) test (ASTM, 2000). Before bringing the RO membranes online, operators can perform pretreatment testing to ensure a feedwater SDI of consistently less than 5.0.

The rapid sand filter of the RO Unit 126 consists of a 650-liter steel tank filled with silica sand and anthracite media. The rapid sand filter is operated with an influent pressure of 3.5 to 4.0 bar and with head losses up to 1.5 bar. The filter is backwashed when the head loss reaches 1.5 bar.

With reference still to FIG. 1, the RO unit 126 has a 1-1 membrane vessel configuration with three membrane elements in each membrane vessel. The elements are preferably Koch/Fluid Systems 4820HR Spiral Wound Thin Film Composite membranes. The membranes are operated at a feed pressure of 9 to 11 bar. RO membrane fouling rate is calculated from measurements taken by flow and pressure instruments on the RO skid. The water permeation coefficient, A, can be calculated using the NORMPRO software provided by Koch/Fluid Systems.

To understand the operation of the Reverse Osmosis unit 126, imagine two columns containing liquid and interconnected with a semipermeable membrane separating the liquids. If one liquid contains more minerals than the other, the natural force referred to as osmosis would cause the liquid containing less minerals to migrate through the membrane into the column with the most minerals. This natural process can be reversed by applying pressure to the column with the most minerals causing its liquid to be forced through the membrane leaving the mineral ions behind. If the membrane is sufficiently impermeable to mineral ions, the permeate or water in the low mineral side of the membrane will be deionized, and the water in the high mineral side will become a more and more concentrated brine. In a continuous process the ratio of the volume of permeate to volume of brine may be called the concentration factor which is commonly on the order of 10 or 20 permeate to 1 of brine.

In furtherance of the present embodiment, two products are generated by the RO unit 126: pure water and a high-salinity concentrate containing concentrated minerals and possibly small amounts of any soluble organic matter in the water presented to the RO unit 126. Preferably, the RO Unit 126 is an Expertise S.r.l. Reverse Osmosis Unit, which can be obtained from Expertise S.r.l. of Milan, Italy.

In the prior art, when large volumes of water are being deionized by a RO unit, disposal of the high-salinity concentrate is usually a problem because it contains high concentration of toxic heavy metals such as cadmium or lead, which are closely regulated by governmental agencies in the United States and in many other countries. This problem, however, is not present in the present invention, which is designed to remove and concentrate heavy metals in the inert sludge of the fermentation cells. The brine produced by the Reverse Osmosis Unit 126 is thus free of heavy metals and is more suitable for reuse or disposal.

Note that the permeate or product water should be pure and low in mineral content. Also note that the wastewater treatment and reclamation process of the present embodiment entails primary treatment (removal of settleable solids), secondary treatment (oxidation of dissolved organics), tertiary treatment (removal of major nutrients such as carbon, nitrogen, and phosphorus compounds), quaternary treatment (removal of organic and inorganic toxic compounds and heavy metals) and quinary treatment (removal of salt) of the wastewater. Because of the low cost of the primary treatment, the secondary treatment, the tertiary treatment, and the quaternary treatment, the present embodiment is significantly less expensive than prior art wastewater treatment and reclamation processes. In one study carried out by members of the Environmental Engineering and Health Sciences Laboratory of the University of California at Berkeley, it has been shown that the wastewater reclamation process according to the present invention consumes less than 500 kWh of power and costs less than U.S. $700 to reclaim one million liters of sewage. A detailed cost analysis can be found in the above referenced provisional patent application.

Another advantage of the present invention is that, because of the removal of most heavy metals in the AFP 112 and in the fermentation cells 113, the high-salinity concentrate produced by the Reverse Osmosis Unit 126 is substantially free of heavy metal ions and is thus suitable for cultivation and growth of halophilic algae such as Dunaliella. As illustrated in FIG. 1, the high salinity concentrate is provided to a Halophilic Algae Growth Unit 128 where halophilic algae are cultivated. In the present embodiment, the Halophic Algae Growth Unit 128 is a High-Rate Pond (e.g., a shallow, aerobic, paddle-wheel-mixed raceway pond).

Dunaliella are microscopic motile green halophilic marine algae that have proved to be a valuable commercial aquaculture product. Dunaliella are valuable because they are rich in neutral and polar lipids and in fatty acids. A major neutral lipid is beta-carotene which may constitute up to 8% of a Dunaliella cell's wet weight and is presently valued at more than $500 per kilogram. Polar lipids include monogalactsylglycerol and several other glyserols. Fatty acids include palmitic and 3-transhexadecaonic among others.

Betacarotene is recognized as a metabolic deterrent to cancer because of its ability to quench or absorb free radicals. Free radicals are known to damage DNA replication, interfere with apoptosis and hence increase the probability of cancer inception. The glycerols are synthesized by Dunaliella to maintain an osmotic balance with the external medium which may be several times as concentrated as sea water. When marine algae are consumed by fish and krill their fatty acids are converted to Omega -3 long chain fatty acids now known to be essential for healthy brain development and maintenance.

Yet another advantage of the present invention is that the sewage wastewater is "softened" before reverse osmosis. Algae, growing in shallow High Rate Ponds 114, use bicarbonate ions as their source of carbon, and thus shift the equilibrium pH toward that at which carbonate forms and combines with calcium resulting in precipitation and sedimentation of $CaCO_3$. Removal of $CaCO_3$ "softens" water and minimizes the pretreatment required prior to RO thus extending the useful life of the RO membranes. This further lowers the operational costs of the wastewater treatment process.

While the present invention has been described with reference to a specific embodiment, the description is illustrative of the invention and is not to be construed as limiting the invention. Various modifications may occur to those skilled in the art without departing from the spirit and scope of the invention.

We claim:

1. A method of processing sewage comprising:
   introducing the sewage to the bottom of a fermentation cell designed for sedimentation and methane fermentation of settleable organic solids, the fermentation cell further having sulfate-reducing microorganisms that release sulfides for combining with multivalent metal ions in the sewage to form insoluble and settleable metal sulfide particles;
   removing suspended solids, microorganisms, nutrients, and pathogens from the sewage to produce a disinfected quaternary effluent; and
   from the disinfected quaternary effluent, producing purified water from the disinfected quaternary effluent, wherein the purified water is substantially free of multivalent metal particles.

2. The method of claim 1 further comprising producing a brine having concentrated minerals from the disinfected quaternary effluent, wherein the brine is substantially free of multivalent metal particles.

3. The method of claim 2 wherein the producing step comprises a step of performing reverse osmosis on the disinfected quaternary effluent to produce the purified water and the brine.

4. The method of claim 1 further comprising passing effluent from the fermentation cell to a primary facultative pond having microorganisms therein, wherein the microorganisms in the pond have a negative surface charge for adsorbing multivalent metal ions in the effluent.

5. The method of claim 4 wherein the microorganisms shift the pH of the effluent to precipitate calcium ions from the effluent.

6. The method of claim 4 wherein the microorganisms in the pond comprise algae.

7. The method of claim 1 wherein the removing step comprises a Dissolved Air Flotation process and a Slow Sand Filtration process.

8. The method of claim 1 wherein the removing step comprises a Dissolved Air Flotation process and a microfiltration process.

9. The method of claim 1 further comprising, before the introducing step, removing non-biodegradable solids from the sewage for separate disposal.

10. A method of cultivating algae, comprising:
    removing non-biodegradable solids from sewage for separate disposal;
    after the removing step, introducing the sewage to the bottom of a fermentation cell designed to optimize sedimentation and methane fermentation of settleable organic solids, the fermentation cell having sulfate-reducing organisms that release sulfides for combining with multivalent metal particles in the sewage to form insoluble and settleable metal sulfide particles;
    after the introducing step, passing the sewage from the fermentation cell to an overlaying primary facultative pond containing microorganisms, wherein the microorganisms have a negative surface charge for adsorbing multivalent metal ions in the sewage;
    after the passing step, removing suspended solids, microorganisms, nutrients, and pathogens from the sewage to produce an disinfected quaternary effluent;
    performing reverse osmosis on the disinfected effluent to produce a saline concentrate that is substantially free of multivalent metal particles; and
    cultivating halophilic microorganisms in the saline concentrate.

11. The method of claim 10 wherein the halophilic microorganisms comprise Dunaliella.

12. A method of treating and reclaiming wastewater, comprising:
    introducing the wastewater to the bottom of a fermentation cell designed to optimize sedimentation and methane fermentation of settleable organic solids, the fermentation cell having sulfate-reducing organisms that release sulfides for combining with multivalent metal particles in the wastewater to form insoluble and settleable metal sulfide particles;
    after the introducing step, passing the wastewater from the fermentation cell to an overlaying primary facultative pond containing microorganisms, wherein the microorganisms have a negative surface charge for adsorbing multivalent metal ions in the wastewater;
    after the passing step, removing suspended solids, microorganisms, nutrients, and pathogens in the sewage to produce an disinfected quaternary effluent.

* * * * *